United States Patent
Bresalier et al.

(10) Patent No.: US 10,620,206 B2
(45) Date of Patent: *Apr. 14, 2020

(54) BIOMARKER FOR DETECTING CANCER

(71) Applicant: Board of Regents, The University of Texas System, Austin, TX (US)

(72) Inventors: Robert Bresalier, Missouri City, TX (US); Nachman Mazurek, Houston, TX (US); James C. Byrd, Spring, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 40 days.

This patent is subject to a terminal disclaimer.

(21) Appl. No.: 15/726,123

(22) Filed: Oct. 5, 2017

(65) Prior Publication Data

US 2018/0031560 A1 Feb. 1, 2018

Related U.S. Application Data

(63) Continuation of application No. 14/350,824, filed as application No. PCT/US2012/059567 on Oct. 10, 2012, now Pat. No. 9,810,691.

(60) Provisional application No. 61/545,675, filed on Oct. 11, 2011.

(51) Int. Cl.
*G01N 33/574* (2006.01)

(52) U.S. Cl.
CPC ............ *G01N 33/57419* (2013.01); *G01N 2333/4724* (2013.01)

(58) Field of Classification Search
CPC ............ G01N 33/57419; G01N 33/574
USPC ................................ 435/7.94, 7.23
See application file for complete search history.

(56) References Cited

U.S. PATENT DOCUMENTS

| 9,810,691 B2 * | 11/2017 | Bresalier ......... G01N 33/57419 |
| 2012/0165221 A1 | 6/2012 | Landstein et al. |
| 2012/0244563 A1 | 9/2012 | Kobayashi et al. |

OTHER PUBLICATIONS

Bresalier et al., "A circulating ligand for galectin-3 is a haptoglobin-related glycoprotein elevated in individuals with colon cancer", *Gastroenterology*, 127(3): 741-748, 2004.
Declaration under 37 C.F.R. 1.131 submitted in corresponding U.S. Appl. No. 14/350,824 on Apr. 28, 2017.
Declaration under 37 C.F.R. 1.132 submitted in corresponding U.S. Appl. No. 14/350,824 on Feb. 4, 2016.
Declaration under 37 C.F.R. 1.132 submitted in corresponding U.S. Appl. No. 14/350,824 on Apr. 28, 2017.
Iglesias et al., "Purification and properties of a 0-galactose/N-acetyl-D-galactosamine-specific lectin from *Erythrina cristagalli*", *Eur J Biochem.*, 123(2): 247-252, 1982.
Matsumoto et al., "Clinical application of a lectin-antibody ELISA to measure fucosylated haptoglobin in sera of patients with pancreatic cancer", *Clin Chem Lab Med.*, 48(4): 505-512, 2010.
PCT International Preliminary Report on Patentability issued in International Application No. PCT/US12/59567, dated Apr. 15, 2014.
PCT International Search Report and Written Opinion issued in International Application No. PCT/US12/59567, dated Dec. 6, 2012.

* cited by examiner

*Primary Examiner* — Yan Xiao
(74) *Attorney, Agent, or Firm* — Parker Highlander PLLC

(57) ABSTRACT

Methods for detecting colorectal cancer in a subject by detection of a galactose-containing 40 kDa molecule in a serum sample from the subject. Methods for quantifying the amount of a galactose-containing molecule in a serum sample are also provided.

20 Claims, 6 Drawing Sheets

BIOMARKER FOR DETECTING CANCER

This application is a continuation of U.S. application Ser. No. 14/350,824, filed Apr. 10, 2014, which is a national phase application under 35 U.S.C. § 371 of International Application No. PCT/US2012/059567, filed Oct. 10, 2012, which claims the benefit of U.S. Provisional Patent Application No. 61/545,675, filed Oct. 11, 2011, the entirety of each of which is incorporated herein by reference.

This invention was made with government support under grant numbers CA069480 and CA086400 awarded by the National Institutes of Health. The government has certain rights in the invention.

BACKGROUND OF THE INVENTION

1. Field of the Invention

The present invention relates generally to the field of molecular biology, immunology and oncology. More particularly, it concerns methods for detecting biomarkers linked to the development of cancer.

2. Description of Related Art

Modern medicine has developed an arsenal of therapies that can be brought to bear against cancer. However, a major factor in the effectiveness of such therapies is the stage of the cancer being treated. Late stage cancers and cancer cells that have already metastasized from their site of origin remain difficult to treat and continue to result in high rates of mortality among patients. Hence successful anti-cancer therapy is largely dependent upon early, accurate, diagnosis. Many cancer diagnostic techniques, however, are inaccurate or invasive, reducing the opportunity for early detection and successful treatment. For example, in the case of colorectal cancer the primary diagnostic technique, colonoscopy, is viewed as highly invasive and typically only applied every 5-10 years and only after the age of 50. Thus, there remains a need for accurate and non-invasive techniques for cancer detection.

SUMMARY OF THE INVENTION

In a first embodiment there is provided a method for detecting a colorectal cancer, comprising (a) obtaining a serum sample of a subject; (b) desialylating the serum; (c) contacting the desialylated serum with an antibody that binds haptoglobin or a cancer-associated haptoglobin glycoform to form a complex, wherein the complex comprises the antibody and a galactose-containing molecule; and (d) detecting the galactose-containing molecule on the complex with a detectable lectin that binds galactose, wherein an elevated level of the galactose-containing molecule detected as compared with a control level is indicative of a colorectal cancer. In certain aspects, a method of the embodiments is defined as an in vitro method.

In a further embodiment there is provided a method for detecting a colorectal cancer, comprising (a) obtaining a serum sample of a subject; (b) desialylating the serum; (c) contacting the desialylated serum with an antibody that binds haptoglobin to form a complex, wherein the complex comprises the antibody and a galactose-containing molecule; (d) detecting the galactose-containing molecule on the complex with a detectable lectin that binds galactose; and (e) determining the presence of (or the probability of the presence of) a colorectal cancer based on an elevated level of the galactose-containing molecule detected as compared with a control level. In certain aspects, a method of the embodiments further comprises performing or obtaining the results of one or more secondary tests to determine the presence of a colorectal cancer. For example, the secondary test can be, without limitation, a fecal occult blood test (FOBT), a colonoscopy or a secondary blood test (e.g., a test for levels of carcinoembryonic antigen (CEA) in the blood).

In still a further embodiment there is provided a method for quantifying a galactose-containing molecule in a serum sample comprising (a) obtaining a serum sample of a subject; (b) desialylating serum; (c) contacting the desialylated serum with an antibody that binds haptoglobin to form a complex, wherein the complex comprises the antibody and a galactose-containing molecule; and (d) detecting galactose on the complex with a detectable lectin that binds galactose, thereby quantifying the galactose-containing molecule in the sample.

In certain aspects of the embodiments, step (b) further comprises diluting the serum between about 25-fold and 150,000-fold, 100-fold and 100,000-fold, 1,000-fold and 50,000-fold, or 10,000-fold and 50,000-fold (e.g., at least about 20-fold, 25-fold, 100-fold, 500-fold, 1,000-fold, 5,000-fold, 10,000-fold or 15,000-fold) before desialylating the diluted serum. As used herein "diluting" means mixing of a sample with a larger volume of a second non-sample solution (e.g., water). As used herein "fold dilution" refers to the dilution factor as compared to a serum sample that has not been mixed with any additional solution (i.e., an unadulterated serum sample).

In a further embodiment there is provided a method for detecting a colorectal cancer, comprising (a) obtaining a serum sample of a subject wherein the serum sample has been diluted between 25-fold and 150,000-fold; (b) desialylating the diluted serum; (c) contacting the desialylated serum with an antibody that binds haptoglobin to form a complex, wherein the complex comprises the antibody and a galactose-containing molecule; and (d) detecting galactose-containing molecule on the complex with a detectable lectin that binds galactose, wherein the elevated level of the galactose-containing molecule detected as compared with a control level is indicative of a colorectal cancer.

In still a further embodiment there is provided a method for quantifying a galactose-containing molecule in a serum sample comprising (a) obtaining a serum sample of a subject wherein the serum sample has been diluted between 25-fold and 150,000-fold; (b) desialylating the diluted serum; (c) contacting the desialylated serum with an antibody that binds haptoglobin to form a complex, wherein the complex comprises the antibody and a galactose-containing molecule; and (d) detecting galactose-containing molecule on the complex with a detectable lectin that binds galactose, thereby quantifying the galactose-containing molecule in the sample.

Thus, certain aspects a method is provided for quantifying a galatose contain molecule in a serum sample in accordance with the foregoing embodiments wherein an elevated level of the galactose-containing molecule detected as compared with a control level is indicates that the subject has an elevated risk of colorectal cancer. Thus, in some aspects, a method of detecting colorectal cancer is provided comprising administering at least a second test for colorectal cancer to a subject identified as having a risk for colorectal cancer. For example, the second test can be a blood test, stool test of a colonoscopy.

Thus, in some aspects, obtaining a serum sample comprises obtaining a diluted serum sample. For example, a serum sample can be a sample that has been diluted by at least about 30-fold, 40-fold, 50-fold, 60-fold, 70-fold, 80-fold, 90-fold, 100-fold, 500-fold, 1,000-fold, 10,000-fold or 15,000-fold.

Certain aspects of the embodiments concern obtaining a serum sample of a patient. The serum sample can, for example, be directly obtained by drawing blood from a patient. In certain cases the sample is obtained from a third party (e.g., a doctor or clinic) or is a frozen banked sample.

In certain aspects methods of the embodiments concern desialylating a diluted serum sample. For example, the sample subjected to desialylation can be a sample that has been diluted by about or at least about 25-fold, 30-fold, 40-fold, 50-fold, 60-fold, 70-fold, 80-fold, 90-fold, 100-fold, 500-fold, 1,000-fold, 10,000-fold or 15,000-fold prior to desialylation. A diluted sample can be desialylated by a variety of methods, such as by treatment with an enzyme or a mild acid. For example, a diluted serum sample can be treated with a neuraminidase enzyme (e.g., a *Vibrio cholerae* neuraminidase). In certain aspects, a diluted sample is treated with a mild acid such as $H_2SO_4$, and optionally heating the sample. For example, a diluted serum sample can be treated with 0.5 N $H_2SO_4$, and heated to about or at most about 50° C., 60° C., 70° C., 80° C. for a period of about or at least about 30 min, 60 min or 90 min.

Certain aspects of the embodiments involve contacting a desialylated and diluted serum with an antibody. For example, in some aspects the sample is diluted to between 25-fold and 150,000-fold, 100-fold and 100,000-fold, 1,000-fold and 100,000-fold, 10,000-fold and 100,000-fold or 15,000-fold and 150,000-fold (e.g., about a 20,000-fold dilution) before contacting the serum with an antibody. Thus, in certain aspects a sample is diluted before desialylation, after desialyation or both.

Antibodies for use according to the embodiments include, without limitation, polyclonal and monoclonal antibodies that bind to haptoglobin (e.g., human haptoglobin). For example, the antibody can be an antibody that was raised against a purified human haptoglobin, such as a rabbit polyclonal antisera (e.g., the H-8636 antisera available from Sigma). An anti-haptoglobin antibody, can in some cases, be labeled or immobilized. For example, in some aspects, the antibody is immobilized on a bead (e.g., a magnetic bead) or a surface (e.g., in a well of a plate).

Some aspects of the embodiments involve a step of washing a complex comprising the antibody and a galactose-containing molecule with a wash solution (i.e., contacting the complex with a volume of wash solution). For example, washing a complex comprising the antibody and a galactose-containing molecule can comprise washing the complex 1, 2, 3, 4 or more times with a solution comprising a physiological amount of salt and a physiological pH, such as PBS. Optionally a wash solution can comprise a detergent such as TWEEN-20 (e.g., about 0.01% to about 0.1% TWEEN-20).

In further aspects, methods of the embodiments concern detecting a galactose-containing molecule on a complex (i.e., a complex comprising an antibody and a galactose-containing molecule) with a detectable lectin that binds galactose. For example, detecting a galactose-containing molecule can comprise (i) contacting the complex with a lectin that binds galactose and (ii) detecting the bound lectin. In certain aspects, the method further comprises (i) contacting the complex with a lectin that binds galactose, (ii) washing the complex 1, 2, 3, 4 or more times with a wash solution; and (iii) detecting the bound lectin. Examples of lectins for use according to the embodiments include, without limitation mammalian galectin-3, *Ricinus communis* lectin, *Datura stramonium* lectin, *Erythrina cristagalli* lectin, or *Lycopersicon esculentum* lectin. In some aspects, the lectin is labeled with a detectable label. In still further aspects, the lectin can be detected with a labeled lectin-binding moiety (e.g., a labeled lectin-binding antibody).

The skilled artisan will recognize that the methods for detecting a lectin will depend on the type of label that is employed. For example, in some aspects, a lection comprises an affinity label (e.g., biotin) and the label is itself detected by the binding of a further molecules linked to a reporter (e.g., avidin linked to a reporter). In further aspects, a lectin may itself be labeled with a reporter. Reporter molecules for use according to the embodiments include, without limitation, dyes, fluorophores, radionuclides and enzymes. For example, in certain aspects, the reporter is a enzyme, such a peroxidase, that amplifies the detection signal by virtue of its catalytic activity.

Some aspects of the embodiments concern detecting a colorectal cancer by detecting an increased level of a galactose-containing molecule. In certain aspects, detecting an increased level of the galactose-containing molecule comprises detecting a relative or absolute increase the level of the molecule. Further aspects of the embodiments concern quantifying a galactose-containing molecule in a serum sample. For example, a galactose-containing molecule can be quantified by comparing an amount of lectin binding to a known reference sample or a panel of reference samples having known concentration a galactose-containing molecule (e.g., samples with known concentrations of asialo-haptoglobin). In certain aspects, such reference samples are assayed simultaneously with the serum sample. However, in some aspects, the reference sample values may be comprised in a reference table.

In further aspects a method of the embodiments further comprises identifying a subject as having a colorectal cancer or at risk of having a colorectal cancer if the subject is determined to have an elevated level of a galactose-containing molecule as compared with a control level. In certain aspects, identifying the subject further comprises reporting that the subject has a colorectal cancer; is at risk of having a colorectal cancer or has an elevated level of a 40-kDa galactose-containing molecule. For example, the reporting can comprise providing a written, oral or electronic report. In some aspects, a report is provided to the tested subject, to a health care provider (e.g., a doctor), or to an insurance company.

In yet a further embodiment there is provided a method for monitoring the effectiveness of an anti-cancer therapy comprising determining the level of a galactose-containing molecule (i.e., a molecule that binds to an anti-haptoglobin antibody) in a sample from a subject treated with an anti-cancer-therapy in accordance with the embodiments. In some aspects, if the levels of the galactose-containing molecule are elevated as compared to a reference level the subject is in need of additional anti-cancer therapy. Conversely, if the level the galactose-containing molecule not elevated as compared to a reference level the subject is not in need of additional anti-cancer therapy. Thus, in certain aspects, a method is provided for monitoring the effectiveness of an anti-cancer therapy comprising (a) determining the levels of a galactose-containing molecule in a sample from a subject before and after treatment with an anti-cancer therapy; and (b) identifying the subject as responsive to the therapy or not responsive to the therapy based on the change in levels of the galactose-containing molecule. For example, the level of a galactose-containing molecule in a responsive patient should be reduced after therapy. In further aspects, a patient identified as not responsive to the first anticancer therapy can be administered a second anti-cancer therapy.

In some embodiments there is provided a method of treating a subject comprising administering an anticancer therapy to a subject identified as a having a colorectal cancer by a method of the embodiments. For example, the anticancer therapy can be a surgical, radiation, chemotherapeutic, or targeted anticancer therapy.

In still a further embodiment, there is provided a kit comprising at least a first haptoglobin-binding antibody (e.g., the H-8636 antisera) and a galatose-binding lectin (e.g., *Erythrina cristagalli* lectin). In certain aspects, the antibody and/or the lectin is bound to a support or to a detectable label. In a further aspect, a kit of the embodiments comprises a desialylating reagent such as a neuraminidase enzyme or a mild acid, such as a $H_2SO_4$. Further reagents that can be included in a kit of the embodiments include, without limitation, a microtiter plate, a detectable label, a lectin-binding antibody, and a dilution buffer (e.g., PBS or water).

It is contemplated that any method or composition described herein can be implemented with respect to any other method or composition described herein. Likewise, aspects of the present embodiments discussed in the context of a method quantifying are equally applicable to method for diagnosing or detecting according to the embodiments.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
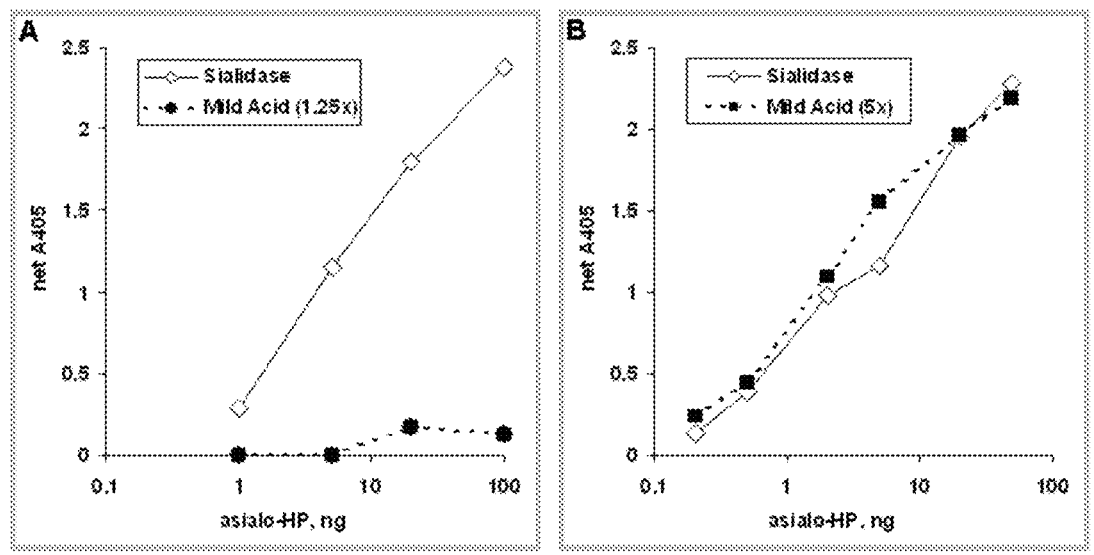
FIG. 1: A, Sandwich ELISA of asialohaptoglobin prepared by neuraminidase vs. mild acid hydrolysis at 1.25× dilution. B, Sandwich ELISA of asialohaptoglobin prepared by neuraminidase vs. mild acid hydrolysis at 5× dilution.

Embodiments of the invention provide a sensitive and reproducible assay for the detection of colorectal cancer. In particular, the inventors have identified a detectable form of a glycoprotein (40-kDa) that binds to anti-haptoglobin antibodies, but is distinct from other human haptoglobin glycoforms, and that is elevated specifically in patients with colorectal cancer. Because the protein appears to present at some level in healthy patients and is immunologically related to haptoglobin the inventors have developed techniques that allow for quantitative detection only of specific glycosylated forms of the 40-kDa protein. The assay involves obtaining a diluted serum sample from patient and treating the bulk sample to desialylate proteins that are present. The desialylated and diluted serum sample is then subjected to a highly sensitive sandwich ELISA assay by capturing the 40-kDa protein using an anti-haptoglobin antibody and detecting the captured protein with a detectable lectin that binds to galactose. By using a desialylated serum sample that has been diluted to between 100-fold and 50,000-fold the assay allows for the amount of the 40-kDa glycoform in a sample to be determine quantitatively. An increased level of the 40-kDa glycoform (e.g., as compared to a control sample or a reference level) is indicative of the presence of colorectal cancer in the patient.

The assay systems and methods provided offer significant advantages over conventional methods for detecting colorectal cancer. For example, whereas a colonoscopy is typically only performed one every 5-10 years due to its cost and invasive nature, the blood tests of the embodiments could be repeated as often as desired by a physician, such as every year, twice a year or even every month. Moreover, such small sample volumes are required for the tests detailed here that portions of blood taken for other purposes could be tasked for use in the assay. The ability to repeat these tests frequently and their exquisite sensitivity offer the opportunity to detect cancers at a very early stage and thus to apply therapy at a time when it can be most effective in improving patient outcome.

I. Immunological Reagents

In certain aspects of the invention, one or more antibodies are employed that bind to the 40-kDa haptoglobin glycoform. Antibodies include any type of antibody, and specifically refer to antibodies that react immunologically with human haptoglobin or immunologically related proteins such as the 40-kDa haptoglobin glycoform. In particular, these antibodies may be used in various diagnostic applications, such as the ELISA assay methods detailed below.

As used herein, the term "antibody" is intended to refer broadly to any immunologic binding agent such as IgG, IgM, IgA, IgD and IgE. The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production. The invention thus provides monoclonal antibodies of the human, murine, monkey, rat, hamster, rabbit and even chicken origin. Due to the ease of preparation and ready availability of reagents, murine monoclonal antibodies will often be utilized.

The methods for generating monoclonal antibodies (MAbs) generally begin along the same lines as those for preparing polyclonal antibodies. Briefly, a polyclonal antibody is prepared by immunizing an animal with, for example a human haptoglobin (e.g., a purified haptoglobin) composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia or synthetic compositions.

Adjuvants that may be used include IL-1, IL-2, IL-4, IL-7, IL-12, interferon, GM-CSF, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants include complete Freund's adjuvant (a non-specific stimulator of the immune response containing killed Mycobacterium tuberculosis), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as -interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography. Thus, in certain aspects, polyclonal antibodies for used according to the embodiments are purified antibodies, such an IgG fraction of antibodies.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells. In some embodiments, however, the antibody that reacts immunologically with the anti-tumor antigen antibody and/or the anti-tumor antigen antibody are present endogenously in a subject.

The methods for generating monoclonal antibodies (MAbs) generally begin along the same lines as those for preparing polyclonal antibodies. Rodents such as mice and rats are often used, however, the use of rabbit, sheep or frog cells is also possible.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions.

One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The favored selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in E. coli.

II. Lectins

It has long been known that extracts from certain plants could agglutinate red blood cells. Although the term "lectin" was originally a term used to describe agglutinins which could discriminate among types of red blood cells. However, the term is used more defined as sugar-binding proteins from a wide variety of sources. Lectins have been found in plants, viruses, microorganisms and animals. Although lectins share the common property of binding to defined sugar structures, their roles in various organisms are not likely to be the same and remain incompletely understood.

Because of the specificity that each lectin has toward a particular carbohydrate structure, even oligosaccharides with identical sugar compositions can be distinguished or separated. Some lectins will bind only to structures with mannose or glucose residues, while others may recognize only galactose residues. Some lectins require that the particular sugar be in a terminal non-reducing position in the oligosaccharide, while others can bind to sugars within the oligosaccharide chain. Some lectins do not discriminate between alpha and beta anomers, while others require not only the correct anomeric structure but a specific sequence of sugars for binding. The affinity between a lectin and its receptor may vary a great deal due to small changes in the carbohydrate structure of the receptor.

Thus, lectins can be used in similar detection methods as antibodies, for the detection of specific carbohydrate moieties. Embodiments of the present invention provide assays for the detection of a 40-kDa haptoglobin glycoform using lectins as selective binding agents. Generally, the carbohydrate composition of the 40-kDa glycoform is exploited in order to detect its presence in a sample. For example, embodiments of the methods of the invention employ galactose-binding lectins to capture or detect the 40-kDa protein comprising such a galactose moiety.

In the study detailed here, the inventors used galactose binding lectins to detect the 40-kDa glycoform in desialylating the diluted serum. Lectins that were found to be effective include mammalian galectin-3, *Ricinus communis* lectin, *Datura stramonium* lectin, *Erythrina cristagalli* lectin, and *Lycopersicon esculentum* lectin. Of these however, the highest specificity was achieved with *Erythrina cristagalli* lectin.

In some aspects, lectins for use according to the embodiments are labeled. Methods for labeling antibodies can generally also be applied to lectins and are further detailed below.

III. Antibody and Lectin Conjugates

The present invention further provides antibodies and lectins reactive with human haptoglobin and the 40-kDa haptoglobin glycoform, that are linked to at least one agent to form an antibody or lectin conjugate. In order to increase the efficacy of such conjugates as diagnostic agents, it is conventional to link or covalently bind or complex at least one desired molecule or moiety. Such a molecule or moiety may be, but is not limited to, at least one reporter molecule. Any antibody or lectin of sufficient selectivity, specificity or affinity may be employed as the basis for a conjugate. Such properties may be evaluated using conventional immunological screening methodology known to those of skill in the art. It will therefore be understood that embodiments referring to antibody conjugates are thus equally applicable to lectin conjugates and vice versa.

A. Conjugation

Thus, in certain aspects a lectin antibody of the embodiments is conjugated to a reporter. Any of a wide array of conjugation schemes can be employed to linkage of an antibody of lectin to a reporter as further detailed below.

An exemplary hetero-bifunctional cross-linker contains two reactive groups: one reacting with primary amine group (e.g., N hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or lectin) and through the thiol reactive group, the cross-linker, already tied up to the first protein, reacts with the cysteine residue (free sulfhydryl group) of the other protein (e.g., the reporter). In some cases, it is preferred that a cross-linker having reasonable stability in serum samples will be employed. Numerous types of disulfide-bond containing linkers are known that can be successfully employed to conjugate targeting and therapeutic/preventative agents. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1988). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Antibodies or lectins may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

B. Reporter Molecules

A reporter molecule is defined as any moiety which may be detected using an assay. Non-limiting examples of reporter molecules which have been conjugated to antibodies or lectins include enzymes, radiolabels, haptens, fluorescent labels, phosphorescent molecules, chemiluminescent molecules, chromophores, luminescent molecules, photoaffinity molecules, colored particles or ligands, such as biotin.

In the case of radioactive isotopes that can be conjugated to antibodies (or lectins) for diagnostic applications, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. Radioactively labeled antibodies of the present invention may be produced according to well-known methods in the art. For instance, antibodies or lectins can be iodinated by contact with sodium and/or potassium iodide and a chemical oxidizing agent such as sodium hypochlorite, or an enzymatic oxidizing agent, such as lactoperoxidase. Antibodies or lectins according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of conjugate contemplated in the present invention are those where the antibody or lectin is linked to a secondary binding ligand and/or to an enzyme (an enzyme tag) that will generate a colored product upon contact with a chromogenic substrate.

Examples of suitable enzymes include urease, alkaline phosphatase, (horseradish) hydrogen peroxidase or glucose oxidase. Secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Likewise, in certain applications it is desirable to immobilize and antibody on a solid surface. For example, antibodies can be absorbed to the surface of the wells of a plate. Such absorption can rely on non-specific interactions with the polymers of the plate or can involve specific binding of the antibodies (e.g., by protein A). In certain aspects antibodies are covalently linked to surface, for example by UV-cross linking.

Optical imaging with dyes also permit visualization of biological activities (Blasdel et al., 1986; Grinvald et al., 1988; Kauer et al., 1988; Lieke et al., 1989). Dyes that are sensitive to physicochemical environments (such as pressure, cell membrane potential, ion concentration, acidity, partial pressure of oxygen, etc.), are subject to changes in absorption or emission of light. The resulting changes act as optical probes to transform biological activities into optical signals that can be converted into optical images.

Water soluble dyes are particularly well suited, including acid dyes, basic dyes, direct dyes, and so on, and equivalents thereof. The dye composition may be prepared as a dry material for ease of storage and packaging. If prepared as a dry composition, prior to usage the composition may be prepared as a solution using a suitable liquid, including water and various organic solvents, or mixtures thereof and so on, by techniques well known to those skilled in the art.

Dyes include methylene blue, Tartrazine (CI 19140), Quinoline Yellow (CI 47005), Eosin (CI 45380), Acid Phloxine (CI 45410), Erythrosine (CI 45430), Sunset Yellow FCF (CI 15985), Acid Violet 5B (CI 42640), Patent Blue AF (CI 42080), Brilliant Cyanine 6B (CI 42660), Acid Brilliant Blue FCF (CI 42090), Naphthalene Green VSC (CI 44025) and Acid Blue Black 10B (CI 20470); and direct dyes such as Paper Yellow GG (CI Direct Yellow 131), Direct Scarlet 4BS (CI 29160), Congo Red (CI 22120), Violet BB (CI 27905), Direct Sky Blue 5B (CI 24400), Patent Blue Violet, Sulfan Dye), Pentamine, guajazulen blue Pentamine, Phthalocyanine Blue (CI 74180), Black G (CI 35255) and Deep Black XA (CI Direct Black 154). The CI number in the description above indicates the identification number in the Color Index, 3rd Ed., The Society of Dyers and Colorists, Bradford, Yorkshire (1971). Preferred dyes include Isosulfan blue or other dye which travels through the lymphatic system.

Chromophores include Fluorescein, Rhodamine, Acid Fuchsin; Acridine Orange; Acridine Red; Acridine Yellow; Alizarin Red; Allophycocyanin; Astrazon Brilliant; Astrazon Orange R; Astrazon Red 6B; Astrazon Yellow; Bodipy Fl; Bodipy TMR; Bodipy TR; Calcein; Calcein Blue; Calcium Green; Calcium Orange; Calcofluor White; Cascade Blue; Flazo Orange; Fluorescein Isothiocyanate (FITC); Fura-2; Fura Red; Genacryl Brilliant Red B; Genacryl Brilliant Yellow 10GF; Genacryl Pink 3G; Genacryl Yellow SGF; Granular Blue; Lucifer Yellow CH; Lucifer Yellow VS; LysoSensor Blue DND-192, DND-167; LysoSensor Green DND-153, DND-189; LysoTracker Green; LysoTracker Yellow; LysoTracker Red; Magdala Red; Magnesium Green; Magnesium Orange; Mitotracker Green FM; Mitotracker Orange; Nile Red; Nuclear Fast Red; Nuclear Yellow; Oregon Green 488; Oregon Green 500; Oregon Green 514; Phorwite AR; Phorwite BKL; Phorwite Rev; Phorwite RPA; Pontochrome; Blue Black; Procion Yellow; Pyrozal Brilliant; Rhodamine Green; Rhodamine Red; Rhodol Green Fluorophore; Rose Bengal; Sevron Brilliant Red 2B; Sevron Brilliant Red 4G; Sevron Brilliant Red B; Sevron Orange; Sevron Yellow L; Texas Red; Thiozol Orange; True Blue; and Xylene Orange.

IV. Immunodetection Methods

In certain embodiments, the present invention concerns immunodetection methods for binding, purifying, removing, quantifying and/or otherwise generally detecting biological components such as a 40-kDa haptoglobin glycoform. Some immunodetection methods include enzyme linked immunosorbent assay (ELISA), radioimmunoassay (RIA), immunoradiometric assay, fluoroimmunoassay, chemiluminescent assay and bioluminescent assay to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In general, the immunobinding methods include obtaining a sample suspected of containing a 40-kDa haptoglobin glycoform, and contacting the sample with a first antibodies that react immunologically with the 40-kDa glycoform in accordance with the present invention, as the case may be, under conditions effective to allow the formation of immunocomplexes.

These methods include methods for purifying a 40-kDa haptoglobin glycoform tissue or organism's samples. In these instances, the antibody removes the 40-kDa protein (and haptoglobin) that react immunologically with antibody. The antibody will preferably be linked to a solid support, such as in the form of a column matrix or the well of a plate, and the sample suspected of containing the 40-kDa haptoglobin glycoform will be applied to the immobilized antibody. The unwanted components will be washed from the column, leaving the antigen immunocomplexed to the immobilized antibody.

The immunobinding methods also include methods for detecting and quantifying the amount of the 40 kDa haptoglobin glycoform in a sample and the detection and quantification of any immune complexes formed during the binding process. Here, one would obtain a sample suspected of containing an antigen, and contact the sample with an antibody against the antigen, and then detect and quantify the amount of immune complexes formed under the specific conditions.

In terms of antigen detection, the biological sample analyzed may be any sample that is suspected of containing an antigen, such as, for example, a tissue section, or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts may be used.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antibodies that react immunologically with anti-tumor antigen antibodies present. After this time, the sample-antibody composition, such as a tissue section, ELISA plate or dot blot, will generally be washed to remove any nonspecifically bound protein species.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody or lectin employed in the detection may itself be linked to a detectable label, wherein one would then simply detect this label, thereby allowing the amount of the primary immune complexes in the composition to be determined. Alternatively, the first antibody or lectin that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody or lectin is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as cancer wherein a specific tumor antigen is expressed, and wherein antibodies exist that react immunologically to an anti-tumor antigen antibody Here, a biological and/or clinical sample suspected of containing a specific disease associated antibody is used. However, these embodiments also have applications to non-clinical samples, such as in the titering of antigen or antibody samples, for example in the selection of hybridomas.

In the clinical diagnosis and/or monitoring of patients with various forms a disease, such as, for example, colorectal cancer, the detection of a cancer specific antigens that react and/or an alteration in the levels of such an antigen, in comparison to the levels in a corresponding biological sample from a normal subject is indicative of a patient with cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

ELISAs

As detailed above, immunoassays, in their most simple and/or direct sense, are binding assays. Certain immunoassays are the various types of enzyme linked immunosorbent assays (ELISAs) and/or radioimmunoassays (RIA).

In some aspects of the invention, there are ELISA assays, including in kits, to test samples of subjects that are suspect or at risk for the development of colorectal cancer. In one exemplary ELISA, the anti-haptoglobin antibodies of the invention are immobilized onto a selected surface exhibiting protein affinity, such as a well in a polystyrene microtiter plate. Then, a test composition suspected of containing the antigen, such as a diluted clinical sample, is added to the wells. After binding and/or washing to remove non-specifically bound immune complexes, the bound antigen may be detected. Detection can be achieved by contacting the sample with a galactose-binding lectin that is linked to a detectable label. This type of ELISA is a "sandwich ELISA". Detection may also be achieved by the addition of a galatose-binding lectin, followed by the addition of a further antibody that has binding affinity for the lectin, with the further antibody being linked to a detectable label.

In a further exemplary ELISA, the galactose-binding lectins of the invention are immobilized onto a selected surface exhibiting protein affinity, such as a well in a polystyrene microtiter plate. Then, a test composition suspected of containing the antigen, such as a diluted clinical sample, is added to the wells. After binding and/or washing to remove non-specifically bound immune complexes, the bound antigen may be detected. Detection can be achieved by contacting the sample with a haptoglobin-binding antibody that is linked to a detectable label. Detection may also be achieved by the addition of a haptoglobin-binding antibody, followed by the addition of a further antibody that has binding affinity for the haptoglobin-binding antibody (e.g., a secondary antibody), with the further antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either lectin or antibody (e.g., an anti-haptoglobin antibody), one will generally incubate the wells of the plate with a solution of the lectin or antibody, either overnight or for a specified period of hours, such as for 4, 5, 6, 7, 8, 9 or 10 hours. Likewise, the incubation can be performed at a specified temperature, such as between about 1° C. and 22° C., e.g., at 4° C. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

After binding of a lectin or antibody to the well, coating with a non-reactive material to reduce background, and washing to remove unbound material, the immobilizing surface is contacted with the biological sample to be tested under conditions effective to allow immune complex (antigen/antibody) formation. For example, the reaction could be incubated for 1, 2, 3, 4, or more hours at room temperature. Detection of the immune complex then requires a labeled secondary binding ligand (e.g., a lectin) or antibody, or a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. For example, the inclusion of a detergent such as 0.01 to 0.1% TWEEN-20 can significantly reduce nonspecific background.

The "suitable" conditions also mean that the incubation is at a temperature or for a period of time sufficient to allow effective binding. Incubation steps are typically from about 1 to 2 to 4 hours or so, at temperatures preferably on the order of 20° C. to 27° C., or in some cases overnight at about 4° C. or so.

Following all incubation steps in an ELISA, the contacted surface is washed so as to remove non-complexed material. A particular washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the lectin, second or third antibody will have an associated label to allow detection. In some cases this will be an enzyme that will generate color development upon incubating with an appropriate chromogenic substrate. In certain aspects the label is an affinity label such a biotin and detection can be achieved by further contact with a detectable affinity molecules (e.g., a labeled avadin). Thus, for example, one will desire to contact or incubate the first and second complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1: 40-kDa Haptoglobin Glycoform Detection by ELISA

Assay Format

Initial results were obtained using a Western blot format to quantify a 40-kDa haptoglobin glycoform and galectin-3 ligand in sera, however this format was not suitable for a diagnostic assay. For example, disadvantages of initial assay include that it was very time-consuming and did not yield a linear response that could be used to quantify the 40 kDa haptoglobin glycoform in a sample, i.e., 40-kDa band density was not directly proportional to amount of the glycoform. Likewise the Western blot assay exhibited gel-to-gel variability and required a known positive cancer serum as a common reference serum, which is not practical for scale-up.

Figure 2:
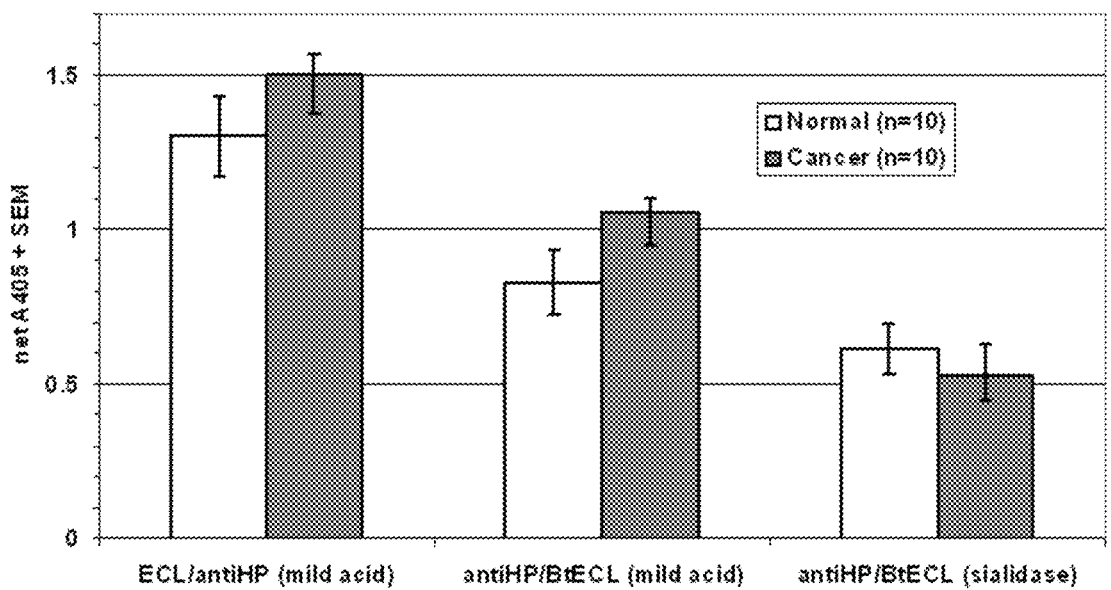
FIG. 2: Comparison of assay formats. Known serum samples, desialylated by mild acid hydrolysis at 5× dilution, were assayed with *Erythrina cristagalli* lectin (ECL) catcher and anti-haptoglobin tracer or with anti-haptoglobin tracer and biotinyl-ECL tracer. Neuraminidase-treated serum samples were assayed in parallel.

A sandwich assay was developed to allow measurement of the 40-kDa glycoform in a complex background by immobilizing ligand with a "catcher" antibody or lectin and detecting the ligand with a "tracer" antibody or ligand. Two complementary sandwich ELISA formats using anti-haptoglobin and lectin were extensively evaluated. A sandwich enzyme-linked immunosorbent assay using lectin catcher and anti-haptoglobin tracer was employed in early developmental studies. However, the alternative sandwich ELISA, using anti-haptoglobin catcher and lectin tracer was found to be superior in discriminating known cancer sera from normal specimens, and was therefore selected for further development and clinical validation (FIG. 2).

Lectin Selection

Initial attempts were made to develop a lectin/anti-haptoglobin sandwich ELISA assay using biotinyl-galectin-3. Although biotinyl-galectin-3 was effective for detection of the 40-kDa glycoform on Western blots, it was not sufficiently sensitive to use as a reagent for the sandwich ELISA. It was found that the failure of biotinyl-galectin-3 to bind to asialohaptoglobin in a microplate format reflected a loss of carbohydrate binding, and was not due to gross degradation of galectin-3 or to inability of secondary reagents to detect biotinyl-galectin-3.

Preliminary studies indicated that *Erythrina cristagalli* lectin (ECL) had a specificity similar to the mammalian lectin galectin-3. Therefore, ECL was used to develop a sandwich ELISA. Both the ECL/anti-haptoglobin and anti-haptoglobin/biotinyl-ECL formats detected asialo-haptoglobin in serum samples, but the anti-haptoglobin/biotinyl-ECL sandwich ELISA was more specific for known cancer specimens. Other beta-galactoside-specific plant lectins that were tested included those from *Ricinus communis, Sophora japonica, Datura stramonium*, and *Lycopersicon esculentum*. However, none of these appeared superior to ECL (Table 1).

TABLE 1

Sensitivity and specificity of beta-galactoside specific lectins in sandwich ELISAs.

| Lectin | Sensitivity | Specificity | Accuracy |
|---|---|---|---|
| *Erythrina cristagalli* | 70% | 50% | 60% |
| *Ricinus communis* | 40% | 40% | 40% |
| *Datura stramonium* | 60% | 60% | 60% |
| *Lycopersicon esculentum* | 40% | 60% | 50% |

One key step necessary for the successful development of the sandwich ELISA is the method used for desialylation. Various studies were undertaken to address the necessity for desialylation, the relative efficacy of neuraminidase enzyme vs. mild acid, and the effect of dilution prior to mild acid treatment.

Desialylation

Initial studies established that desialylation was necessary for binding of galectin-3 to the 40 kDa glycoform, but a desialylation procedure need to be developed that could yield quatitaive assay results. In developing the sandwich ELISA, it was found that desialylation was necessary for binding of ECL to haptoglobin. Initially, desialylation was performed either with *Vibrio cholerae* neuraminidase digestion or with mild acid hydrolysis (0.1 N $H_2SO_4$, 60 min at 80° C.) with minimal dilution (1.25-fold). Sandwich ELISAs, using either ECL/anti-haptoglobin or anti-haptoglobin/ECL indicated that the neuraminidase digestion gave at least a 10-fold higher signal than the mild acid hydrolysis treatment (FIG. 1). Therefore, early assays of known cancer and normal sera were performed using neuraminidase digestion, but there was difficulty in getting reproducible results.

To further develop the desialylation method, the loss of antigenicity of haptoglobin caused by mild acid treatment was studied in detail. Direct binding assays established that this was due to loss of binding of anti-haptoglobin to the mild-acid-treated glycoprotein. Some of this loss of antigenicity could be due to concentration-dependent aggregation, thus, the mild acid treatment was repeated at higher dilutions (5-fold, 25-fold, and finally 100-fold dilution). With the mild acid hydrolysis performed at higher dilutions, signal was equivalent to that obtained with neuraminidase digestion, with a higher specificity for cancer sera (FIG. 2). Desialylation by mild acid hydrolysis at a 100-fold dilution was therefore used in clinical method validation.

Additional Element of the ELISA

Two different anti-haptoglobin antibodies were evaluated for potential use in sandwich ELISA, a polyclonal anti-haptoglobin and a mouse monoclonal anti-haptoglobin. The two antibodies gave similar results in the ECL/anti-haptoglobin sandwich ELISA format, but only the polyclonal anti-haptoglobin could practically be used in the anti-haptoglobin/biotinyl-ECL format.

Concentrations of anti-haptoglobin used as catcher, or biotinyl-ECL used as tracer, and of ABC complex were varied to ensure they were not limiting. In addition, the effects of blocking with a commercial block solution rather than with bovine serum albumin (BSA) and of diluting sera in PBS rather than PBST, was studied, however, BSA and PSBT were found to be superior. Extensive studies with known cancer sera and known normal sera were also performed to determine the optimal 20,000-fold dilution of desialylated serum that would fall within the linear range of the assay.

Example 2: Detailed 40-kDa Haptoglobin Glycoform Detection Protocol

Mild Acid Hydrolysis and Dilution:
For initial sample preparation the following steps were used:

Serum or plasma specimens were thawed (aliquotted in small volumes (0.3 ml), then stored at −80° C.).

5 µl samples of coded serum were collected. Residual aliquots were marked as once-thawed, and return excess to −80° C.

Samples were added to 395 µl water in 1.5 ml tube and mixed.

100 µl 0.5 N $H_2SO_4$ was added and mixed with the diluted samples.

Samples were heated for 60 min at 80° C. and then cooled on ice.

100 µl 10×PBS was added and mixed with the samples.

100 µl 0.5 N NaOH was added and mixed with the samples.

300 µl of water was added and mixed with the samples

The pH of the samples were checked (with pH paper) and recorded.

Resulting 200-fold diluted desialylated serum samples were refrozen in 200 µl aliquots at −20° C.

Three aliquots are used on separate days for ELISA. Two aliquots are reserved.

Preparation of Anti-Haptoglobin Coated Plates:
Day 1
Four 96-well microtiter plates were marked with triplicate wells inside for serum specimens, PBST blanks and normal asialohaptoglobin standards. Typical plate geometry is shown in Table 2.

100 µl Rabbit anti-haptoglobin (Sigma Catalog # H-8636) was diluted into 25 ml PBS and 50 µl was added to each well of four microtiter plates. The plate is left overnight at 4° C.
Day 2
Anti-haptoglobin is decanted and discarded. Excess liquid is removed by striking inverted plate on paper towels. Each well is then washed once with PBS using a squeeze bottle. The wash is decanted and discarded. Again excess liquid is removed by striking inverted plate on paper towels.

200 µl of 1% BSA in PBS (prepared fresh daily) was added to each well and the components left for 60 min at room temp. (Meanwhile, final dilutions of standards, unknowns, and controls were prepared)

BSA/PBS was decanted and discarded. Excess liquid is removed by striking inverted plate on paper towels.

Final Dilutions of Standards, Unknowns, and Controls.

Final dilutions of coded desialylated serum were produced by thawing fresh aliquots of 56 coded specimens of 200-fold diluted desialylated serum. 5 µl samples were taken and the residual aliquot was marked as once-thawed, and return to −20° C. The 5 µl sample added and mixed with to 495 µl of PBST on ice in a 500 µl tube to give 20,000-fold final dilution relative to serum.

Final dilution of known positive and negative specimens were produced by thawing re-frozen aliquots of 2 known positive cancer specimens (200-fold diluted desialylated serum) or re-frozen aliquots of 2 known negative normal specimens (200-fold diluted desialylated serum), respectively. 10 µl samples were removed from each specimen and the residual aliquots returned to −20° C. The 10 µl samples were each added to and mixed with 990 µl PBST on ice in 1.5 ml tubes to give 20,000-fold final dilution relative to serum.

Final dilution of normal asialohaptoglobin standards were produced by thawing 50 µg/ml stock of normal asialohaptoglobin (asHP). After sampling, the residual stock was returned to −20° C. A 20 µl of 50 µg/ml asHP was added and mixed with 1980 µl PBST in 15 ml tube to give 500 ng/ml asHP. A 400 µl sample of 500 ng/ml asHP was added and mixed with 600 µl PBST in 1.5 ml tube to give 200 ng/ml asHP. A 200 µl sample of 500 ng/ml asHP was added to and mixed with 800 µl PBST in 1.5 ml tube to give 100 ng·ml asHP. A 100 µl sample of 500 ng/ml asHP was added to and mixed with 900 µl PBST in 1.5 ml tube to give 50 ng/ml asHP. A 40 µl sample of 500 ng/ml asHP was added to and mixed with 960 µl PBST in 1.5 ml tube to give 20 ng/ml asHP. Finally, a 20 µl sample of 500 ng/ml asHP was added to and mixed with 980 µl PBST in 1.5 ml tube to give 10 ng·ml asHP.

Binding of Analytes and Standards:
50 µl/well of 20,000-fold diluted unknown desialylated serum in PBST was added in triplicate (3×16=48 interior wells/plate).

50 µl/well of 20,000-fold diluted known control sera in PBST was added in triplicate (3×4=12 wells/plate).

50 µl/well of PBST was added to 24 wells (6 interior & 18 exterior) as blanks.

50 µl/well of asHP standards (10 ng/ml, 20 ng/ml, 50 ng/ml, 100 ng/ml, 200 ng/ml, & 500 ng/ml) was added, in triplicate (3×6=18 exterior wells/plate).

Typical plate geometry is shown in Table 2.

The plate is incubated for 1 h at room temp. (Meanwhile, 1 ug/ml biotinyl *Erythrina cristagalli* lectin is prepared in PBST.)

Excess liquid was removed and discarded from the plate by striking the inverted plate on paper towels.

Each well was washed once with PBST (using a squeeze bottle). Excess liquid was removed and discarded by striking the inverted plate on paper towels.

Biotinyl Lectin Binding
50 µl/well of 1 µg/ml biotinyl *Erythrina cristagalli* lectin in PBST was added.

The plate was incubated for 1 h at room temp. (Meanwhile, the Avidin-Biotin-Complex were prepared)

Excess liquid is removed and discarded by striking the inverted plate on paper towels.

Each well is washed with PBST a 1st time (using a squeeze bottle). Excess liquid from the 1st wash is removed by striking inverted plate on paper towels.

Each well is washed with PBST a second time (using a squeeze bottle). Excess liquid from the 2nd wash is removed by striking inverted plate on paper towels.

Each well is washed with PBST a third time (using a squeeze bottle). Excess liquid from the 3rd wash is removed by striking inverted plate on paper towels.
Preparation of Avidin-Biotin Complex
A VECTASTAIN® ABC Reagent Kit (Vector Elite PK-6100) is used for detection.
10 drops of REAGENT A (Avidin DH) was added to 25 ml PBST, then 10 drops of Reagent B (Biotinylated Horseradish Peroxidase) was added.
Reagents were mixed and allowed to stand 30 min at room temp.
Detection of Biotinyl Lectin Bound
50 µl/well of Avidin-Biotin Complex was added.
The plate was left for 1 h at room temp. (Meanwhile, the ABTS reagent is prepared.)
Excess liquid was removed and discardedby striking inverted plate on paper towels.
Each well is washed with PBST a 1st time (using a squeeze bottle). Excess liquid from the 1st wash is removed by striking inverted plate on paper towels.
Each well is washed with PBST a second time (using a squeeze bottle). Excess liquid from the 2nd wash is removed by striking inverted plate on paper towels.
Each well is washed with PBST a third time (using a squeeze bottle). Excess liquid from the 3rd wash is removed by striking inverted plate on paper towels.
100 µl/well ABTS reagent (0.03% $H_2O_2$, 1 mM 2,2-azino-di(3-ethylbenzthiazoline) sulfonate in 0.1 M citrate, pH 4.0). was added and the time noted.
The plate is incubated for exactly 30 min at room temp.
The plate is read A405 on Dynex Technologies MRXTC ELISA reader.
Calculations
For each plate, the median blank was subtracted from gross A405 of standards, controls, and unknowns. A regression line was constructed for each plate with the 1 ng to 10 ng standards (ignoring 0.5 ng and 25 ng standards) to use for mg/ml calculations. For each plate, mg/ml concentrations are calculated for each unknown and control median net A405 values from triplicate wells using regression line. Median net A405 values from triplicate wells were used to calculate mg/ml for each unknown. Any excessive plate-to-plate variation in the blank, standards, or known controls was noted.
Each serum was assayed on 3 separate plates on separate days (in batches of 4 plates). For each serum, the mg/ml results of 1st assay (sequential order of samples), 2nd assay (shuffled order), and 3rd assay (scrambled order) were presented individually, along with median and the mean, SD, and SEM of the mg/ml results. Any excessive day-to-day variation in blank, standards, or known controls was noted.

Reagents for Assays
Rabbit anti-haptoglobin AB: Sigma catalog # H-8636.
BSA: bovine serum albumin Sigma catalog # A-3059
Biotinyl ECL: Vector catalog # B-1145
Vectastain Avidin Biotin Complex (ABC kit): Vector Elite PK-6100
PBS: (137 mM NaCl, 2.7 mM KCl, 8.1 mM $Na_2HPO_4$, and 1.5 mM $KH_2PO_4$). 10×PBS prepared inhouse.
PBST: PBS with 0.05% TWEEN-20 [Sigma Catalog # P3563]
Asialohaptoglobin standard: 500 µl 1 mg/ml haptogobin [Sigma catalog # H-3536] in water was added to 300 µl water in 15 ml tube and mixed. 200 µl 0.5 N $H_2SO_4$ was added and mixed. Mixture was heated for 60 min at 80° C. and cooled on ice. 1 ml 10×PBS was added and mixed. 200 µl 0.5 N NaOH was added and mixed. 8.8 ml water was added, mixed and the pH of the resulting solution checked for neutralization with pH paper. The resulting 50 µg/ml asialohaptoglobin standard in was frozen in 200 µl aliquots at −20° C.
ABTS reagent: 0.03% $H_2O_2$, 1 mM 2,2-azino-di(3-ethylbenzthiazoline) sulfonate in 0.1 M citrate (pH 4.0): 30% hydrogen peroxide [Sigma catalog # H-1009] (diluted 1000-fold for ABTS reagent); 100 mM ABTS in water [Sigma catalog # A-1888] (store frozen in 500 µl aliquots; diluted 100-fold for ABTS reagent); 1 M citrate pH 4.0 (dilute 10-fold for ABTS reagent).

Example 3: Assessment of Assay Sensitivity, Specificity and Reproducibility

The high through-put ELISA assay detailed above takes advantage of similarities in ligand binding between galectin-3 and the lectin *Erythrina cristagalli*. This sandwich ELISA was used to compare 150 blinded sera samples from the Early Detection Research Network (EDRN) colon reference set (normal controls, adenomas and adenocarcinomas). Results of the assays were used to constructed receiver operating characteristic curves of sensitivity versus (1-specificity). The curves shown in FIG. 3 demonstrated that the assay successfully differentiated individuals with colorectal neoplasia from normal controls with a high degree of sensitivity and specificity.
The AUC for the galectin-3 (Gal3) ligand alone, normal versus cancer, was 0.84 and for Gal3 ligand+FOBT (fecal occult blood test) was 0.91 (FOBT alone 0.62). The AUC for Gal3 ligand alone, normal versus all neoplasia (adenoma+ carcinoma), was 0.74 and for Gal3 ligand plus FOBT normal versus all neoplasia was 0.80. Thus, based on a newly developed assay, the serum 40-kDa haptoglobin glycoform (and galectin-3 ligand) shows promise for validation as a

TABLE 2

Typical ELISA Plate Geometry

Figure 4:
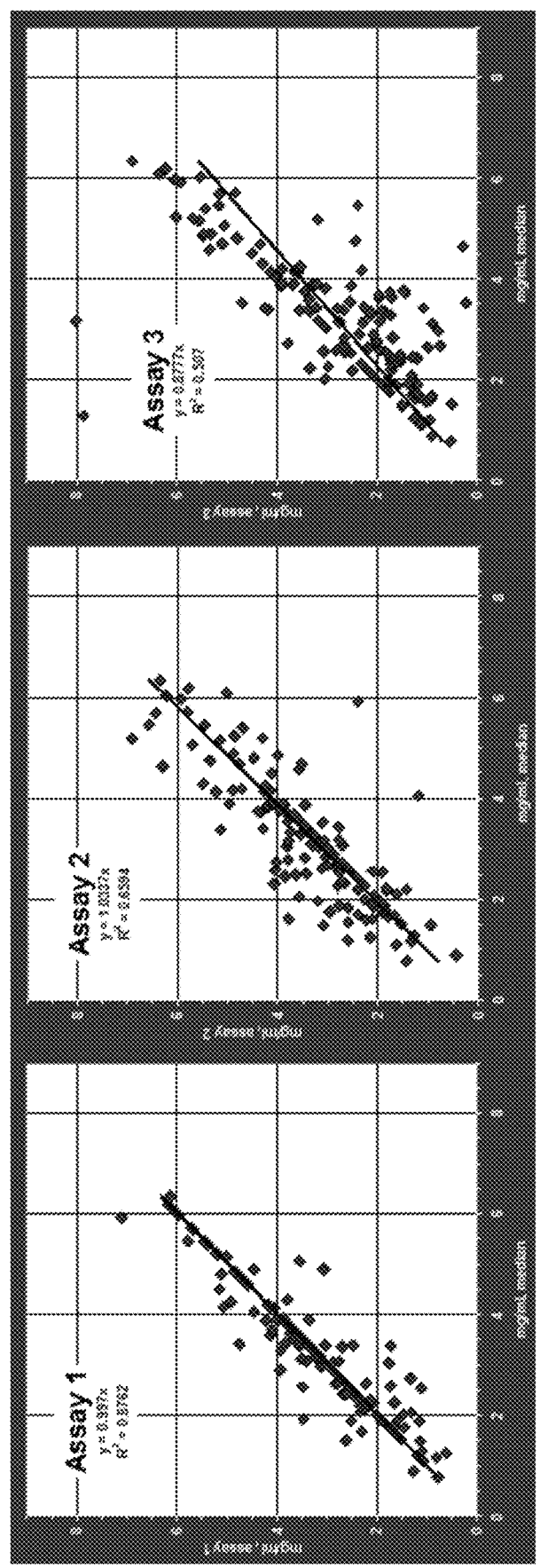
FIG. 4: Quantitative ELISA detection of the 40-kDa haptoglobin glycoform is highly reproducible. Graphs show assay of serum samples assayed on 3 separate plates (with serum order sequential, shuffled, or scrambled) on separate days (3 sets of 11 plates each in batches of 3 or 4 plates). Net A405 values were used to calculate mg/ml for each assay set (y-axis), which is compared to the median mg/ml for each serum (x-axis).
Figure 5:
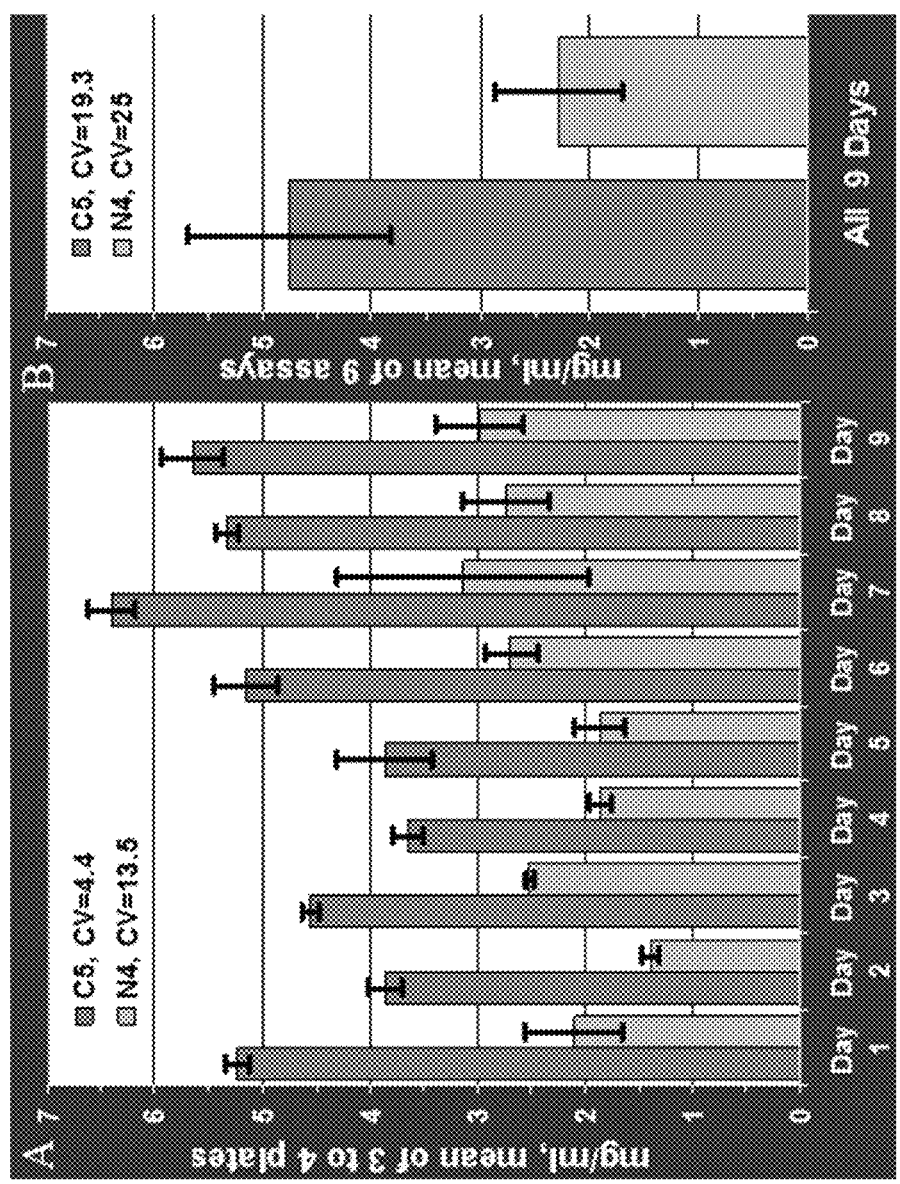
FIG. 5: Graphs show assay of serum samples of separate days (A). Each plate had triplicate reference standard of 20,000-fold diluted mild acid-treated colon cancer serum (EDRN #73249037, local name C5) and normal serum (EDRN #73265650, local name N4). B shows the mean of the assay in A.

| IV | 1 | 2 | 3 | 4 | 5 | 6 | 7 | 8 | 9 | 10 | 11 | 12 |
|---|---|---|---|---|---|---|---|---|---|---|---|---|
| A | PBST | | | 10 ng/ml asHP | | | 20 ng/ml asHP | | | 50 ng/ml asHP | | |
| B | PBST | | C8 | | T31 | | | T32 | | | PBST | |
| C | | | N8 | | T33 | | | T34 | | | | |
| D | | | T35 | | T36 | | | T37 | | | | |
| E | | | T38 | | T39 | | | T40 | | | | |
| F | | | T41 | | T42 | | | C5 | | | | |
| G | | | T43 | | T44 | | | N4 | | | | |
| H | 100 ng/ml asHP | | | 200 ng/ml asHP | | | 500 ng/ml asHP | | | PBST | | | clinically relevant biomarker for detection of colorectal neoplasia. The ELISA was validated within and between days using calibration curves and concentration reproducibility. Each unknown serum was assayed on 3 separate plates on 3 separate days. These data demonstrate that the assay is linear to 500 pg. Analytic samples assayed on three different days were within a coefficient of variability of 15% (see, e.g., FIG. 4). Day to day variation in assay results were assessed in more detail in the studies shown in FIG. 5. As shown, while absolute quantitation of serum 40-kDa haptoglobin glycoform varied slightly from day to day, discrimination between cancer and control samples was maintained in all cases.

Figure 6:
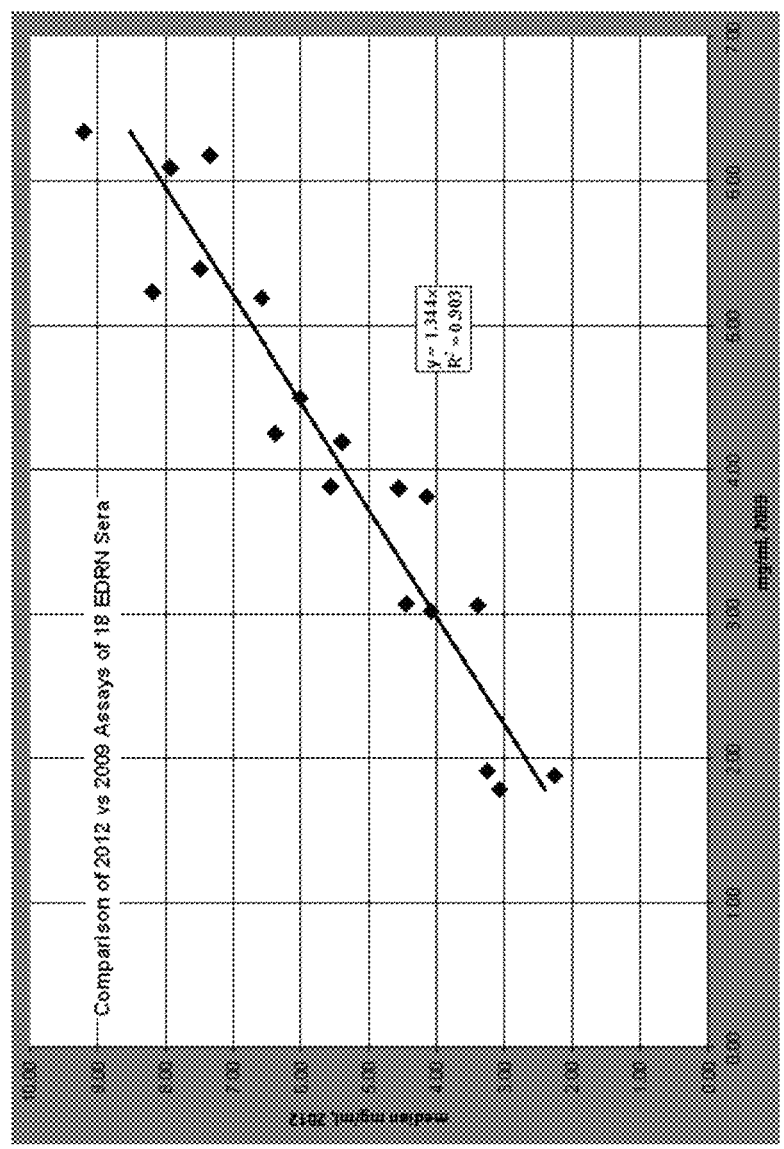
FIG. 6: Protein concentrations as assessed by a method of the embodiments from samples assayed in 2009 (x-axis) versus 2012 (y-axis).

It was further demonstrated that assay results remained consistent over time and when samples were stored (frozen) for extended periods of time prior to being subjected to assay. As shown in FIG. 6, samples were quantitively assessed for the 40-kDa serum haptoglobin glycoform and then stored for three years prior to reassessment. Despite the storage time and the time elapsed between assays the 40-kDa glycoform levels from the original assay and the reassessment correlated well. These studies demonstrate not only that accurate results can be obtained from stored frozen samples, but also that the assay system was highly reproducible.

Example 4: High Throughput Assay Modification

In order to adapt the assay for use in a high throughput format the ELISA based system was modified for use with beads. For one coupling reaction, 100 µL of uncoupled magnetic beads (MC10026-01 Bio-plex Pro Magnetic COOH Beads, Region 26, 1 mL, BioRad) at the concentration of $1.25 \times 10^7$ beads/mL were put into a tube, after a vortex (Baxter S♦P→Vortex Mixer) and sonicate (mini UltraAsonik™ Ney) steps. The tube was positioned in a magnetic separator containing a strong magnet for 1 min. Then, the supernatant had to be delicately removed and 100 µL of wash buffer (PBS, 0.05% TWEEN-20, pH 7.4) were added to the uncoupled beads. The mixture was positioned in the magnetic separator for 1 min. and the supernatant was discarded. The uncoupled beads were then resuspended in 80 µL of activation buffer (0.1 M $NaH_2PO_4$, pH 6.2). 10 uL of fresh 50 mg/mL S-NHS (Thermo Scientific, Prod #24510) in activation buffer are added to the tube followed by the fresh addition of 10 uL of 50 mg/mL EDC (Thermo Scientific, Prod #22980). The beads were activated 20 min. at RT under agitation and in the dark. After that, activated beads were washed twice with 150 µL of PBS with a high speed mix for 10 sec. after each wash. Between each wash, the supernatant was removed after 1 min. in the magnetic separator. The activated beads were resuspended with 100 µL of PBS, and 9 µg of anti-haptoglobin antibody diluted in PBS were added into the tube. The total volume was brought to 500 uL with PBS and the activated beads were incubated for 2 hr. at RT under agitation and in the dark. After the 2 hr. of coupling, the tube was positioned in the magnetic separator for 1 min. The supernatant was then discarded and the coupled beads were resuspended with 500 µL of PBS. The coupled beads were incubated 30 min. at RT, under agitation and in the dark, with 250 uL of blocking buffer (PBS, 1% BSA, 0.05% Azide, pH 7.4). Finally, the tube was positioned in the magnetic separator for 1 min. and the supernatant was removed. The coupled beads were then resuspended in 650 µL of storage buffer (PBS, 0.1% BSA, 0.02% TWEEN-20, 0.05% Azide, pH 7.4) and the bead concentration was estimated with a hemocytometer.

To a 96-well plate (Greiner bio-one, No. 655096), anti-haptoglobin coupled beads (2500 beads/well) were added. Then, 50 µL of haptoglobin standards or samples were added in each well. The wells were homogenized (Mixer type 16700) and the plate was incubated 1 hr. at RT under agitation and in the dark. After that, the plate was washed twice with PBST (Bio-Plex Pro™ Wash Station). Then, 50 µL of biotinyl-ECL at the concentration of 2.5 mg/mL prepared in staining buffer (PBS, 1%; BSA, pH 7.4) were added to each well. The plate was mixed and was incubated for 1 hr. at RT under agitation in the dark. The plate was then washed three times with PBST and finally, 50 µL of streptavidin-PE (BioRad #171-304501) at the concentration of 2 ug/mL prepared in staining buffer were added to each well. The plate was mixed and incubated for 10 min. at RT under agitation and in the dark. Finally, 75 µL of storage buffer was added to each well and after 2 min. of plate agitation, the streptavidin-PE fluorescence on beads was read by a Bioplex instrument (BioRad, Ca).

Figure 3:
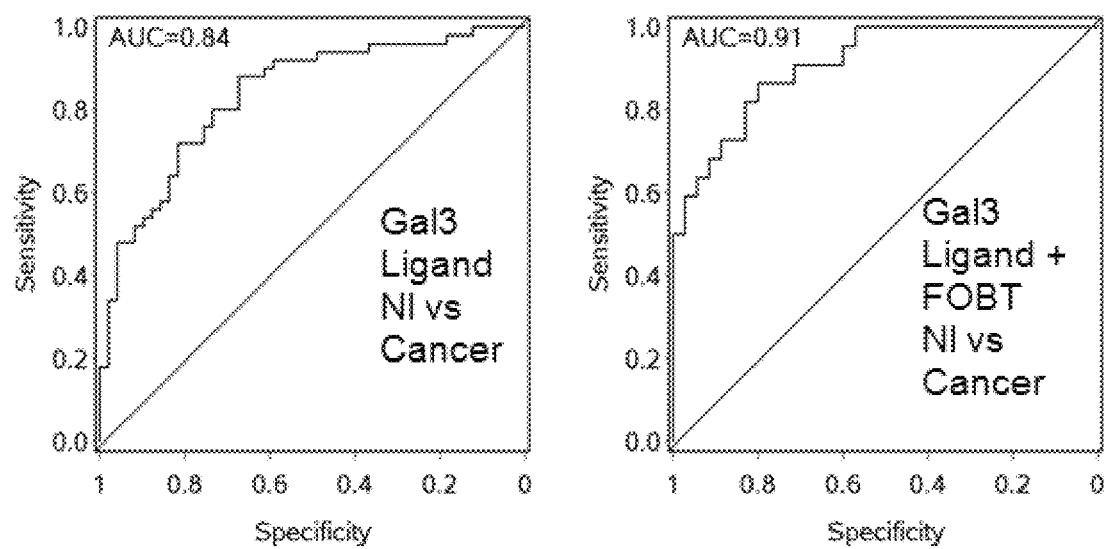
FIG. 3: Constructed receiver operating characteristic curves of sensitivity versus (1-specificity) using a sandwich ELISA of the embodiments. Results demonstrated that the assay successfully differentiated individuals with colorectal neoplasia from normal controls with a high degree of sensitivity and specificity. The AUC for the 40-kDa haptoglobin glycoform (galectin-3 (Gal3) ligand) alone, normal versus cancer, was 0.84 (left panel) and for Gal3 ligand+ fecal occult blood test (FOBT) was 0.91 (right panel).
Figure 7:
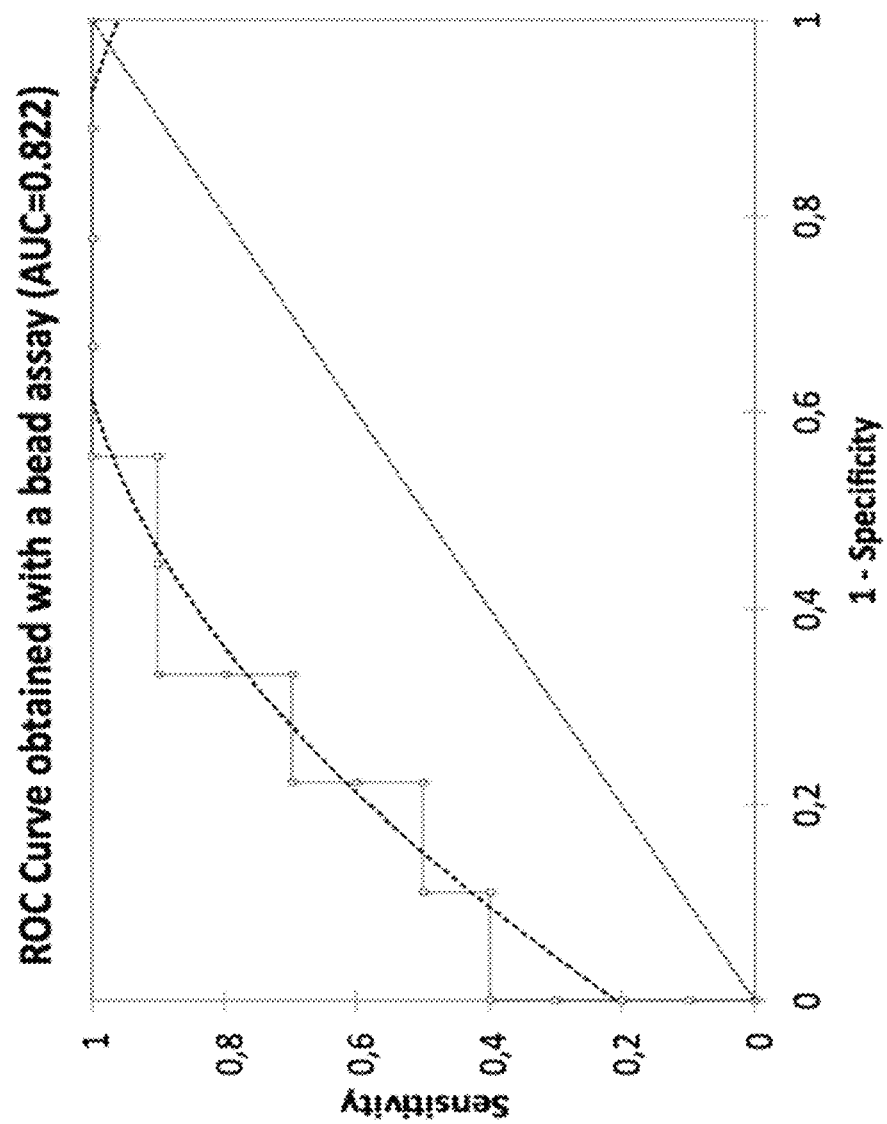
FIG. 7: Constructed receiver operating characteristic curves of sensitivity versus (1-specificity) using a bead-based assay of the embodiments.

As shown in FIG. 7, assays performed on beads resulted in similar specificity and sensitivity as compared to assays completed in wells of microtiter plates (see, e.g., FIG. 3 vs. FIG. 7). Thus, these studies demonstrate that the assays can be replicated on the surface of beads and are thus amenable to further commercial scale-up.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,680,338
U.S. Pat. No. 4,938,948
U.S. Pat. No. 5,141,648
U.S. Pat. No. 5,563,250
U.S. Pat. No. 5,856,456
U.S. Pat. No. 5,880,270
Antibodies: A Laboratory Manual, Cold Spring Harbor Laboratory, 1988
Atherton et al., *Biol. of Reproduction*, 32, 155-171, 1985.
Blasdel and Salama, *Nature*, 321:579, 1986.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
De Jager et al., *Semin. Nucl. Med.* 23(2), 165-179, 1993.
Dholakia et al., *J. Biol. Chem.*, 264, 20638-20642, 1989.
Doolittle and Ben-Zeev, *Methods Mol. Biol.*, 109, 215-237, 1999.
Gefter et al., *Somatic Cell Genet.*, 3:231-236, 1977.
Goding, In: *Monoclonal Antibodies: Principles and Practice*, 2d ed., Orlando, Fla., Academic Press, 60-61, 65-66, 71-74, 1986.
Grinvald et al., *Physiological Reviews*, 68:1285, 1988.
Gulbis and Galand, *Hum. Pathol.* 24(12), 1271-1285, 1993.
Kauer, *Nature*, 331:166, 1988.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Lieke et al., *Annu. Rev. Physiol.* 51:543, 1989.
Nakamura et al., In: *Enzyme Immunoassays: Heterogeneous and Homogeneous Systems*, Chapter 27, 1987.
Owens and Haley, *J. Biol. Chem.*, 259, 14843-14848, 1987.
Potter and Haley, *Meth. Enzymol.*, 91, 613-633, 1983.
Wawrzynczak & Thorpe, *Cancer Treat Res.*, 37:239-51, 1988.

The invention claimed is:

1. A method of treating a subject having colorectal cancer or pre-cancer comprising performing a colonoscopy on the subject after having been determined to have a colorectal cancer or pre-cancer, said method comprising the following steps:
   (a) desialylating a serum sample from the subject; and then
   (b) contacting the desialylated serum sample with an antibody that binds haptoglobin to form a complex; and then
   (c) quantitating the complex with a detectable lectin that binds galactose in order to detect or diagnose colorectal cancer using a quantitative immune-detection assay, wherein the presence of a galactose-containing haptoglobin glycoform is associated with the presence of colorectal cancer, wherein the quantitative immune-detection assay is not a Western blot; and then
   (d) performing a colonoscopy on the subject.

2. The method of claim 1, wherein the detectable lectin that binds galactose is selected from the group consisting of *Ricinus communis* lectin, *Sophora japonica* lectin, *Datura stramonium* lectin, *Erythrina cristagalli* lectin, and *Lycopersicon esculentum* lectin.

3. The method of claim 2, wherein the detectable lectin is *Erythrina cristagalli* lectin.

4. The method of claim 1, wherein the pre-cancer is an adenoma.

5. The method of claim 1, wherein the cancer is a carcinoma.

6. The method of claim 1, further comprising surgical removal of the cancer or precancer.

7. The method of claim 6, comprising the surgical removal of an adenoma.

8. The method of claim 1, said subject having been determined to have a colorectal cancer or pre-cancer by a method further comprising obtaining the level of carcinoembryonic antigen (CEA) in a serum sample from the subject prior to step (d).

9. The method of claim 1, said subject having been determined to have a colorectal cancer or pre-cancer by a method further comprising obtaining the level of galectin-3 ligand in a serum sample from the subject prior to step (d).

10. The method of claim 9, said subject having been determined to have a colorectal cancer or pre-cancer by a method further comprising obtaining the level of carcinoembryonic antigen (CEA) and galectin-3 ligand in a serum sample from the subject prior to step (d).

11. The method of claim 1, wherein step (a) comprises diluting the serum between 25-fold and 50-fold.

12. The method of claim 1, wherein the quantitative immune-detection assay is an enzyme linked immunosorbent assay (ELISA), radioimmunoassay (RIA), immunoradiometric assay, fluoroimmunoassay, chemiluminescent assay or bioluminescent assay.

13. The method of claim 12, wherein the quantitative immune-detection assay is an ELISA.

14. The method of claim 13, wherein the quantitative immune-detection assay is a sandwich ELISA.

15. The method of claim 1, wherein desialylating the serum comprises treating the serum with a mild acid.

16. The method of claim 1, wherein desialylating the serum comprises treating the serum with a neuraminidase.

17. The method of claim 1, wherein the antibody that binds haptoglobin is a polyclonal antibody.

18. The method of claim 1, wherein the antibody that binds haptoglobin is bound to a substrate or a magnetic bead.

19. The method of claim 1, wherein the antibody that binds haptoglobin is a polyclonal antibody raised against purified human haptoglobin.

20. The method of claim 1, further comprising contacting the complex with a wash solution prior to step (c).

* * * * *